United States Patent
Kolowitz et al.

(10) Patent No.: US 10,510,439 B2
(45) Date of Patent: Dec. 17, 2019

(54) SYSTEM AND METHOD FOR PROCESSING HEALTHCARE INFORMATION

(71) Applicant: UPMC, Pittsburgh, PA (US)

(72) Inventors: Brian J. Kolowitz, Pittsburgh, PA (US); James J. Venturella, Jr., Pittsburgh, PA (US); Gonzalo Romero Lauro, Allison Park, PA (US); Vivek Kotha Reddy, Wexford, PA (US); Christopher Ross Deible, Allison, PA (US); Rasu Bickram K Shrestha, Allison Park, PA (US); Veliyan Krasimirov Georgiev, Wexford, PA (US)

(73) Assignee: UPMC, Pittsburgh, PA (US)

( * ) Notice: Subject to any disclaimer, the term of this patent is extended or adjusted under 35 U.S.C. 154(b) by 145 days.

(21) Appl. No.: 14/299,545

(22) Filed: Jun. 9, 2014

(65) Prior Publication Data

US 2015/0356247 A1 Dec. 10, 2015

(51) Int. Cl.
*G16H 10/60* (2018.01)
*G16H 40/20* (2018.01)
*G16H 15/00* (2018.01)

(52) U.S. Cl.
CPC ............ *G16H 10/60* (2018.01); *G16H 15/00* (2018.01); *G16H 40/20* (2018.01)

(58) Field of Classification Search
CPC .......... G06F 19/322–327; G06H 10/60; G06H 15/00; G06H 40/20; G16H 10/60; G16H 15/00; G16H 40/20
See application file for complete search history.

(56) References Cited

U.S. PATENT DOCUMENTS

| | | |
|---|---|---|
| 5,101,476 A | 3/1992 | Kukla |
| 5,146,562 A | 9/1992 | Kukla |
| 5,301,105 A | 4/1994 | Cummings, Jr. |
| 5,964,700 A | 10/1999 | Tallman et al. |
| 5,974,389 A | 10/1999 | Clark et al. |
| 6,347,329 B1 | 2/2002 | Evans |
| 6,463,417 B1 | 10/2002 | Schoenberg |
| 6,684,276 B2 | 1/2004 | Walker et al. |
| 6,983,423 B2 | 1/2006 | Dvorak et al. |
| 7,251,610 B2 | 7/2007 | Alban et al. |
| 7,275,220 B2 | 9/2007 | Brummel et al. |
| 7,461,079 B2 | 12/2008 | Walker et al. |
| 7,725,332 B1 | 5/2010 | Soong |
| 7,865,373 B2 | 1/2011 | Punzak et al. |
| 7,949,545 B1 | 5/2011 | Madras et al. |
| 8,239,218 B1 | 8/2012 | Madras et al. |
| 8,639,520 B2 * | 1/2014 | Finn .................. G06F 19/327 705/2 |
| 2001/0032100 A1 | 10/2001 | Mahmud et al. |

(Continued)

*Primary Examiner* — Sheetal R Paulson
(74) *Attorney, Agent, or Firm* — Tracey Beiriger (57) ABSTRACT

A method for processing healthcare information includes: receiving information related to a patient and a plurality of providers involved with caring for the patient; using the information to generate patient centered provider graphs that describe relationships among the patient and the plurality of providers and include an indication of provider availability within a clinical situation; and presenting the graphs to a plurality of uses. An apparatus that is used to practice the method is also provided.

18 Claims, 4 Drawing Sheets

(56) References Cited

U.S. PATENT DOCUMENTS

| | | |
|---|---|---|
| 2001/0041991 A1 | 11/2001 | Segal et al. |
| 2002/0072933 A1 | 6/2002 | Vonk et al. |
| 2005/0125252 A1 | 6/2005 | Schoenberg |
| 2005/0288965 A1* | 12/2005 | Van Eaton ............. G06Q 50/22 705/2 |
| 2006/0282302 A1* | 12/2006 | Hussain ................ G06F 19/327 705/2 |
| 2008/0052115 A1 | 2/2008 | Spradley et al. |
| 2010/0174555 A1* | 7/2010 | Abraham-Fuchs ... G06F 19/328 705/3 |
| 2010/0187117 A1 | 7/2010 | Lingenfelter et al. |
| 2012/0246741 A1 | 9/2012 | Klotz et al. |
| 2014/0164011 A1* | 6/2014 | Guelich ................ G06F 19/327 705/2 |
| 2015/0031326 A1* | 1/2015 | Begin ................... H04W 24/08 455/405 |

* cited by examiner

SYSTEM AND METHOD FOR PROCESSING HEALTHCARE INFORMATION

BACKGROUND

Field of the Invention

Embodiments of the present invention relate to information systems and methods implemented by those systems, and more particularly to systems and methods for processing healthcare information.

Description of the Related Art

Healthcare information and interactions among healthcare providers are typically managed through a combination of application tools where the providers spend valuable time looking for information, reacting to micro-events, locating individuals, and selecting communicating modes and channels to communicate with other healthcare providers.

Electronic medical record (EMR) systems generally contain partial information. EMR systems are also primarily transactional, whereas outbound notifications such as Health Level Seven (HL7) messages describe specific actions. These systems do not monitor and/or determine relationships between event actions such as viewing of the medical record. In situations where data is spread across systems, providers have to review records within multiple systems to determine who is involved in the care of a patient. This combined transactional information does not capture all of the provider interactions with the patient. The provider is left to connect the dots between the available information and the individuals providing care.

Current communication systems allow for presence within applications but do not communicate that presence across applications and platforms. Tools that do span applications lack the patient and provider relationship context which drives the clinically related provider presence. This can result in providers performing the functions of a micro-event aggregator, filter, notification and decision making system.

SUMMARY

In one embodiment, a method for processing healthcare information includes: receiving information related to a patient and a plurality of providers involved with caring for the patient; using the information to generate patient centered provider graphs that describe relationships among the patient and the plurality of providers and include an indication of provider availability within a clinical situation; and presenting the graphs to a plurality of users.

In another embodiment, an apparatus for processing healthcare information includes: a processing device configured to receive information related to a patient and a plurality of providers involved with caring for the patient, to use the information to generate patient centered provider graphs that describe relationships between a plurality of providers and include an indication of provider availability within a clinical situation, and to present the graphs to a plurality of users.

DETAILED DESCRIPTION

In various embodiments of the invention, the relevant providers involved in the care of a given patient can be identified by the generation of patient centered provider graphs which are relevant to the user's role and patient's condition. The graphs can identify relevant providers involved in the care of a given patient, as well as provider availability and importance within the clinical situation.

Provider availability and importance within the clinical situation can be revealed by displaying clinically related presence across applications and platforms. As used in this description, clinically related presence refers to an individual's availability and/or status with regards to the clinical situation. For instance, a medical assistant may have touched the patient's medical record, which results in the individual being included in the provider graph. In a clinical situation where a provider is attempting to contact another provider, such as a Code Blue, the medical assistant is not relevant to the situation. Examples of clinically related presence include: Critical, Related, and Unrelated. Importance is determined by an ontological mapping of the clinical situation to clinically related presence and the role of involved individuals.

Over-notification of micro-events can be avoided through aggregation, algorithmic analysis, and meta-event generation.

In one embodiment, a clinical social technology dynamically generates patient centered provider graphs that describe relationships between all providers involved in the care of a patient. Clinical social technology allows users to quickly access individuals that are part of a Clinical "Social" Event such as the Code Blue situation described above.

Providers contained within the graph can have direct and/or latent ties with each other and the patient. Latent ties exist technically but have not yet been activated. For instance, a latent tie may exist between an Emergency Room Attending Physician and a Scribe Nurse even though they may not have yet interacted. This latent tie can then be activated if a communication between providers is initiated within the application prior to communication outside of the application. These ties can be revealed through the analysis of provider roles and patient conditions.

A relationship with a patient can be permanent (for example the patient himself/herself and the Primary Care Physician) or transient for a time period related to a specific episode of care (for example an Emergency Department Physician).

Apparatus used to implement the methods described herein can employ a technology framework that utilizes the provider graph, underlying data, and events to facilitate (i) communication between providers and (ii) generate provider specific notification of relevant events.

Figure 1:
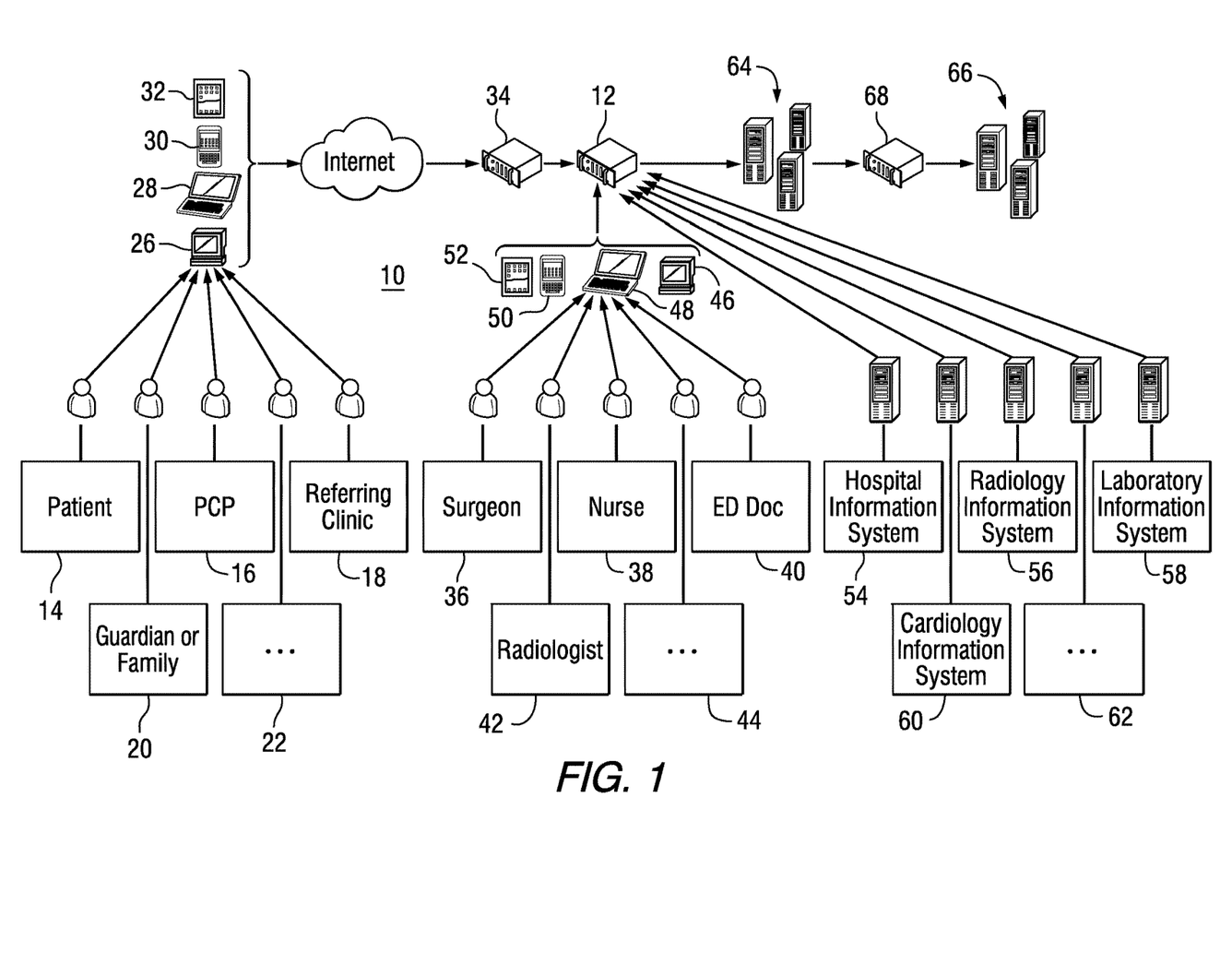
FIG. 1 is a block diagram of elements of a healthcare information system in accordance with an embodiment of the invention.

FIG. 1 is a block diagram of a system 10 that can be used to implement an embodiment of the invention. The system includes a processing device 12 (e.g., a computer or other data processor) that is configured to communicate with a plurality of users and information systems. A first plurality of users, which can include a patient 14, a primary care provider 16, a referring clinic 18, a guardian or family member 20, and/or another user 22 can communicate with the processing device using the Internet 24 or some other network. The users can interact with the system using any of a variety of communication devices, such as for example, a first workstation 26, a first laptop computer 28, a first smart phone 30, or a first tablet computer 32. Such devices can include a keyboard, touch screen, or other means for inputting information and a graphical user interface or other display means for displaying information for the user. A firewall 34 can be included between the Internet or other network and the processing device.

A second plurality of users, which can include a surgeon 36, a nurse 38, an ED doctor 40, a radiologist 42, and/or another user 44, can also communicate with the processing device. These users can interact with the system using any of a variety of communication devices, such as for example, a second workstation 46, a second laptop computer 48, a second smart phone 50, or a second tablet computer 52.

The processing device 12 can also receive information from a plurality of information systems, such as for example, a hospital information system 54, a radiology information system 56, a laboratory information system 58, a cardiology information system 60, and/or some other information system 62.

A load balanced web farm 64 can be used to connect the processing device to a highly available database 66 through a database interface 68.

The processing device 12 can be programmed or otherwise configured to perform the functions described herein. For example, the processing device can generate the patient centered graphs and make those graphs available to the user devices.

Figure 2:
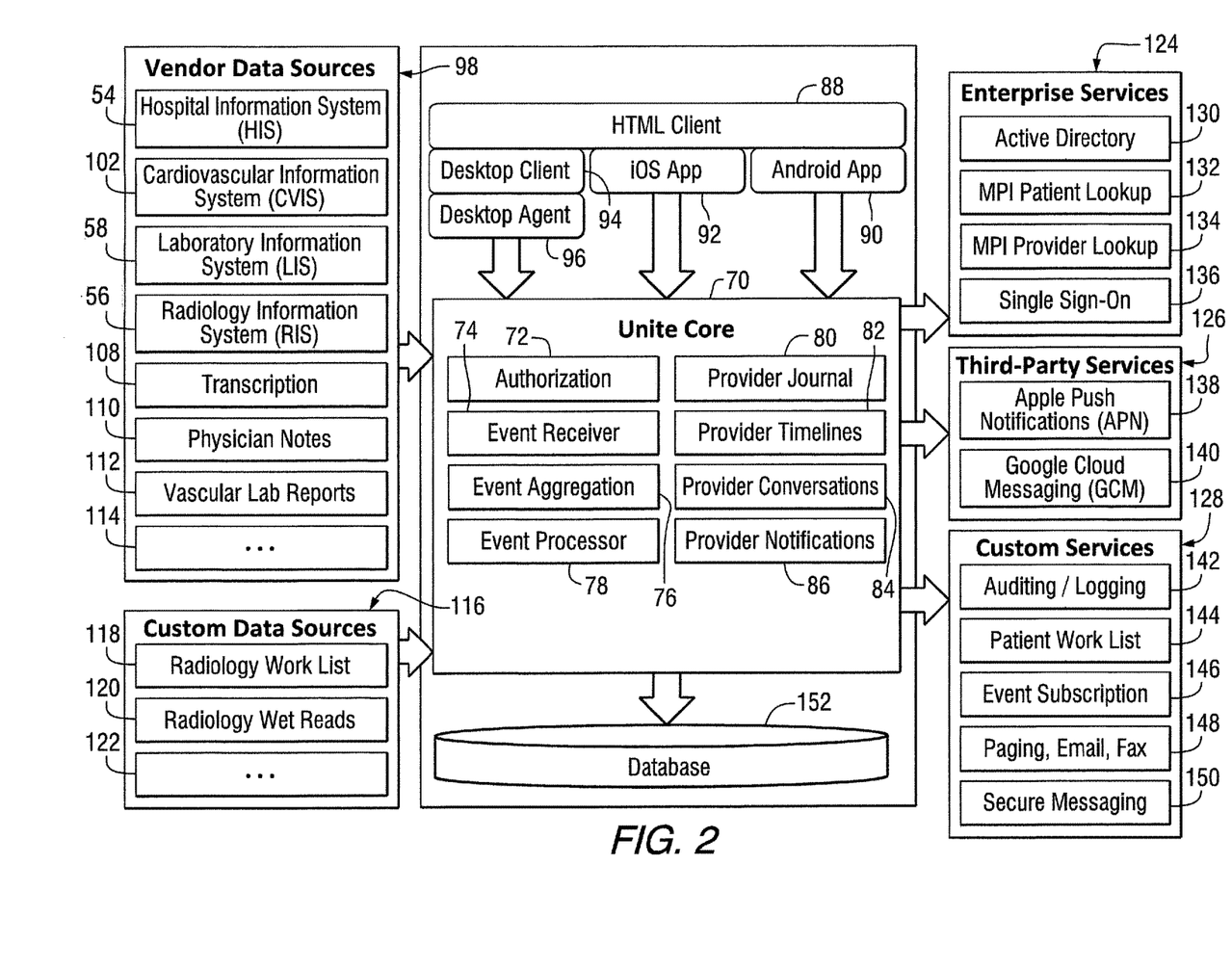
FIG. 2 is a block diagram of the system architecture for a healthcare information system in accordance with an embodiment of the invention.

FIG. 2 is a block diagram of the system architecture for a healthcare information system that can be used to implement an embodiment of the invention. The system of FIG. 2 is shown to include a core software application 70 that can run on the processing device 12 of FIG. 1. The core software includes a plurality of modules including an authorization module 72, an event receiver 74, an event aggregation 76, an event processor 78, a provider journal 80, provider timelines 82, provider conversations 84, and provider notifications 86. The various system users and data sources can interact with the core application through an HTML client 88 that accommodates, for example, an Android application 90, an iOS application 92, and/or a desktop client 94 that can act through a desktop agent 96.

The core software application can receive data from a plurality of vendor data sources 98 that can include, for example, a hospital information system 54, a cardiovascular information system 102, a laboratory information system 58, a radiology information system 56, a transcription service 108, physician notes 110, vascular lab reports 112, and/or other data sources 114. The core software application can receive data from a plurality of custom data sources 116 that can include for example, a radiology work list 118, a radiology wet list 120, and/or another custom data source 122.

The core software application can provide output to a plurality of services, including enterprise services 124, third-party services 126, and/or custom services 128. The enterprise services can include for example, an active directory 130, a Master Patient Index (MPI) patient lookup 132, an MPI provider lookup 134, and/or a single sign-on 136. The MPI is a collection of all known Patient ID's which allows for the cross-referencing and resolution of any ID against another for a particular patient. The MPI system also typically contains a single unique ID that ties all other IDs together.

The third-party services can include for example, Apple push notifications 138, and/or Google cloud messaging 140. The custom services can include for example, auditing/logging 142, patient work lists 144, event subscription 146, paging, email, fax 148, and/or secure messaging 150. A database 152 can store data that is used by, or produced by, the core application.

Figure 3:
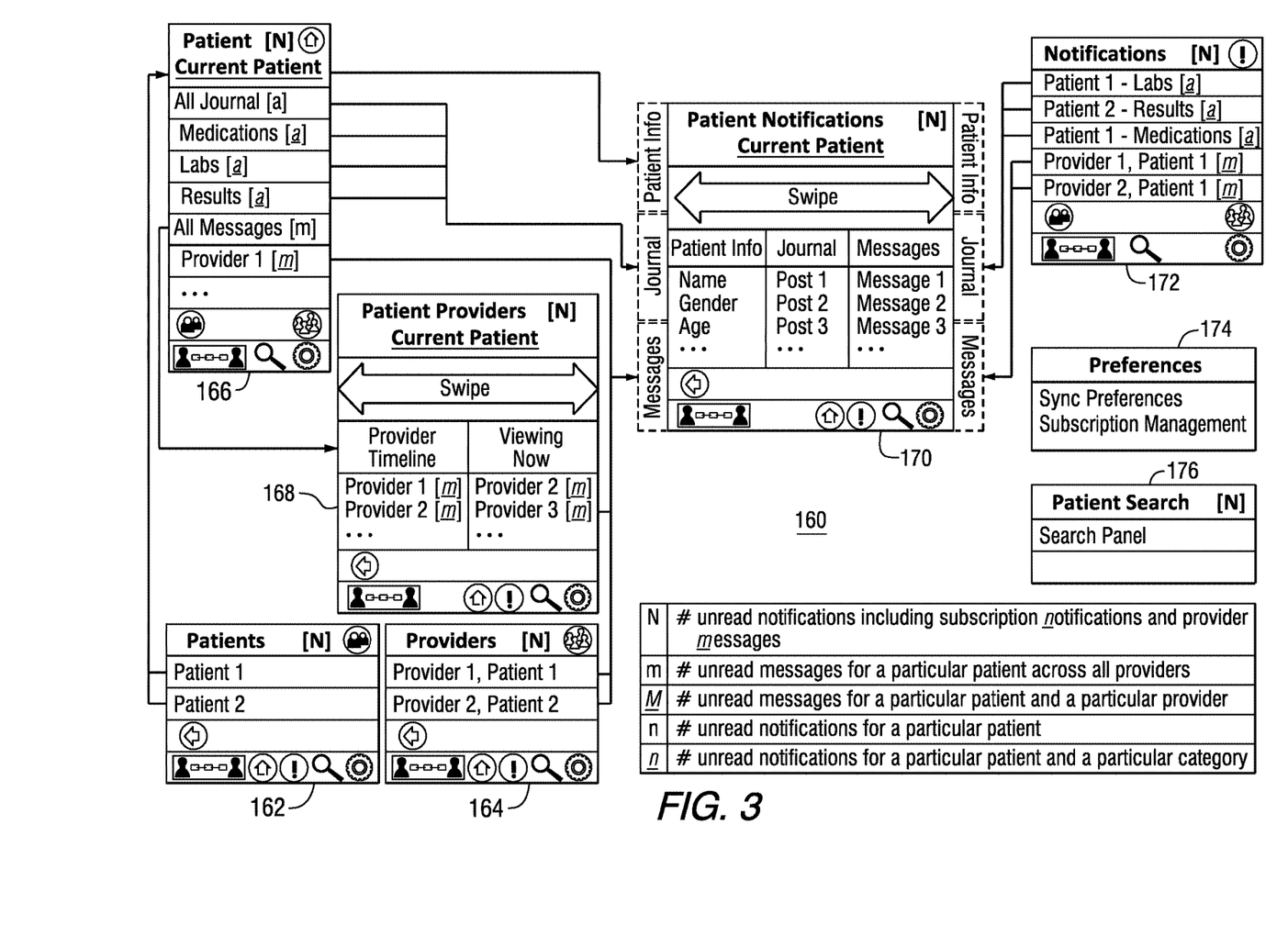
FIG. 3 is a wireframe diagram of a healthcare information system in accordance with an embodiment of the invention.

FIG. 3 is a wireframe diagram that illustrates the framework of a healthcare information system 160 that can be used to implement an embodiment of the invention. The system of FIG. 3 includes a patient database 162; a provider database 164; a patient information database 166 that includes specific information relating to particular patients; a patient provider database 168; and a patient notification system 170; and a notifications database 172. A preferences function 174 and patient search function 176 are also provided.

The patient database includes information relating to a plurality of patients. This information can comprise, for example, journal information including medications, labs and test results. The patient information can also include provider messages relating to a patient. The patient provider database 168 can include a timeline of provider interactions with the patient, as well as a listing of providers who are currently viewing the patient information. The patient notification system can include patient information, journal information and messages relating to the patient. The notifications database can contain various notifications that have been issued relating to a plurality of patients.

The preferences section includes standard application and data synchronization preferences that would be found in any messaging application. Data synchronization preferences include on/off as well as synchronization frequency (e.g. 1 min., 5 min., 15 min, etc.). Subscription Management relates to the user's preference to receive push notification of the meta-events on the device.

Patient Search allows the user to manually look up a patient that is not part of a provider graph for which the user is participating. For instance, a physician might be called for a consult for a patient with whom she or he does not have an existing relationship. In this situation, the user could search by name, medical record number and/or birth date. The result would be a list of patients that matched the search criteria.

In FIG. 3, the word "SWIPE" describes the way in which a user could navigate from screen to screen. For instance, in 168 there are two screens and the user can navigate from screen to screen. For instance, in item 68 there are two screens named Provider Timeline and Viewing Now. Only one screen is visible at any point in time. The user would swipe with a single finger from left to right or right to left to transition screens.

Using the systems illustrated in FIGS. 1-3, a Patient Clinical Context is informed by a Legacy Context, including Electronic Health Record (EHR) data and identity data about both the patient and the user(s). Legacy Context refers to the informational representation of the action taken expressed as an event. For example, legacy context represents actions such as "lab test ordered" for a patient through a singular event. Additionally, a repository of workflow models can provide templates for the workflows executing in the Patient's Clinical Context. The Patient Clinical Context is a knowledge level representation relating the specific informational event to the user's role. For example, the legacy context of "lab test ordered" for a patient is not relevant to all roles such as medical assistant or radiology technologist.

This Patient Centered Context relevant to the clinical situation governs the associations between providers in the graph.

Figure 4:
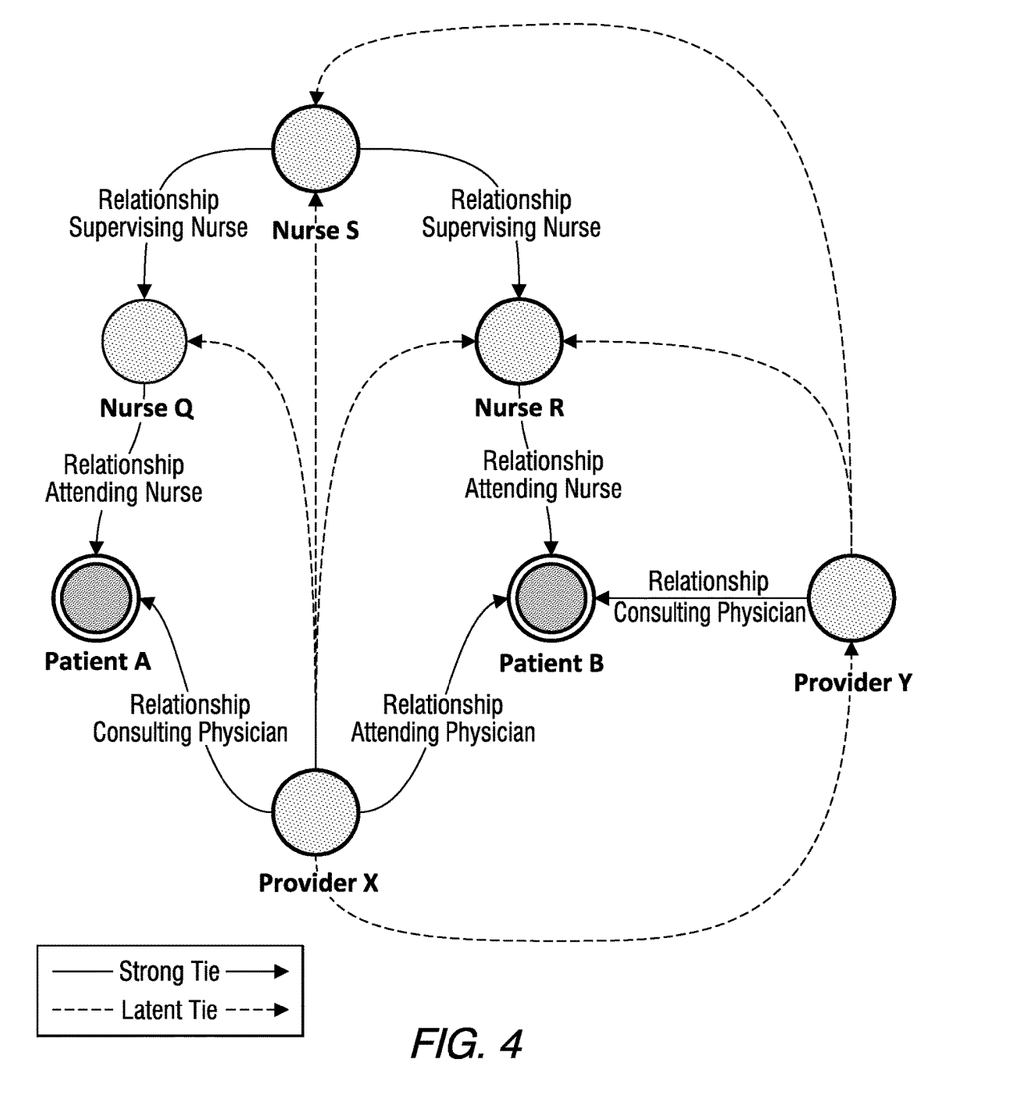
FIG. 4 is a schematic representation of a patient centered provider graph.

FIG. 4 is a schematic representation of a patient centered provider graph. Graphs can be presented as lists within the application. The user (Provider X) selects a patient with whom she or he is associated (Patient B) and sees a list of associated Providers (Nurse R, Nurse S, and Provider Y). Direct relationships are denoted as Strong Ties with solid lines. Latent relationships are denoted with dashed lines. In FIG. 4, Provider X is associated with Nurse S through the Patient B relationship with Nurse R and Nurse R's relationship with supervising Nurse S.

As discussed below, the graphs are combined with presence functionality [0041] to provide an indication of provider availability and importance within a clinical situation.

The processing framework can be configured to capture events through standard interfaces including Health Level Seven (HL7), Digital Imaging and Communications in Medicine (DICOM), and Cross Enterprise Document Sharing (XDS) as well as through direct Application Programming Interface (API) application integration of Hospital Information Systems (HIS) with the processing framework. Events used to generate the patient graph include but are not limited to: admission, discharge, transfer, orders, results, patient context change within systems, and clinical application context change.

Events themselves constitute the conditions that generate the graph. The events are also retained to add context to the relationship. For instance, an HL7 message describing Patient B's hospital admission will contain information identifying Provider X as the attending physician. The association, or interaction, in the graph is formed between Provider X and Patient B. The interaction is all that is needed to describe the graph, but additional context could be gathered by the event.

The patient centered provider graphs can be generated through the detection and analysis of direct and indirect provider interactions with a patient. Direct interactions can be captured through the use of the application in communication or through the analysis of events. For instance, an example of a direct interaction would be the assignment of an attending physician to a patient in the Electronic Medical Record (EMR).

These graphs describe direct and latent ties between providers as well as trust networks in the care team. Trust networks are an information systems theory construct that includes mostly strong ties between similarly valued individuals that interact and share resources, risks, and are accountable for the actions of each other.

Examples of graphs can include: all providers that viewed the patient's record in any application; all providers that viewed the patient's record in any application within the last N minutes; all attending physicians for residents interacting with a particular patient; and/or all specialists that interpreted an exam for a particular patient within an episode of care.

Graphs displayed as filtered lists would be presented based on the user's role. In one embodiment, the user would not be able to select a graph, but could navigate through the filtered list to show higher order relationships which becomes a less filtered version of the graph. Users can show and hide information by role. For instance, users can choose to never display medical assistants in the graph.

The processing framework provides cross-application clinically related provider presence. The clinical presence follows the user across platforms (e.g., mobile, desktop, and web) and adjusts the preferred communication mode according to the currently utilized device. The clinical presence reflects the strengths of the relationships in the provider graph. The relationships are weighted according to the strength clinical relationship. For instance, Provider X (FIG. 4) may have a weight of 1 for Patient B where the weight for Provider Y is 0.5. These weights are used to create presence bands defining Critical, Related, and Unrelated states. A provider with a weak latent tie to the patient can be shown as simply available if the user is online within the application, whereas another provider with a strong relationship to the patient will show as critical and available if the user is online within the application. Presence states include: Critical-Available; Critical-Unavailable; Related-Available; and Related-Unavailable.

Information relating to captured events coupled with processing algorithms can be used to generate the provider graph. In one example, the processing framework generates "meta-events" for the purposes of provider notification. A meta-event is an event that describes a series of other smaller micro-events. In this situation an example meta-event is "Patient Discharge Approval" which relies on the occurrence of a number of smaller micro-events including but not limited to: radiology result available, lab result available, cardiology result available, and attending physician available.

Another example of a meta-event is the notification to a hospitalist to discharge a patient. This meta-event can be generated as an algorithmic compilation of micro-events (e.g. admissions, orders, results, record views, record locks) from specialty systems such as radiology, cardiology, and laboratory with provider role and patient condition. A meta-event notification ties to a clinical action which is a decision point on a clinical pathway. These meta-events can be published to specific event listeners (146 in FIG. 2) or to other custom services (128 in FIG. 2) such as a service bus.

Application specific listeners can be attached to deliver platform specific notifications to for example, a desktop, mobile, and/or web device. Application specific listeners may adopt standard interfaces (124, 126 in FIG. 2) or consist of custom bridge software (128 in FIG. 2) that translates internal application events to external Application Programming Interfaces (APIs) or services.

The application can be deployable, for example, as an Internet/Intranet user Interface, a desktop application and on mobile devices including but not limited to iOS, Android and Windows. The application can be implemented with custom developed software, algorithms, and interfaces for integration with other information systems.

Embodiments of the invention can capture non-transactional events and couple them with transactional events to generate the patient centered provider graph.

Embodiments of the invention can dynamically create lists of relevant providers in a patient-centric context. The strengths of the relationships in the provider graph can be used to provide a clinically related provider presence which informs the user of the relevance of providers according to the clinical situation and user role.

Embodiments of the invention provide a unique ability to track non-transactional events of patients in healthcare information systems as well as the creation of meta-events which can then be used to identify and suggest relevant providers and minimize communication noise. Communication noise in this sense means reducing the amount of inappropriate communications. This is accomplished by providing more relevant and appropriate lists of individuals to communicate with, and indicating their availability. The use of the application also favors less disruptive forms of communication such as sending an instant message over initiating a phone call or grabbing someone in the hallway as they are on their way to see a patient. Meta-events can be leveraged to trigger the delivery of notifications and offer a flexible and customizable mechanism to deliver critical information to providers of care. Users can subscribe to specific notifications or can receive notifications based on their role. Examples of notifications range from alerts of the availability of critical laboratory results or diagnostic reports, to more complex algorithms such as notification that a specialist is locking an exam and preparing to deliver a diagnosis.

Embodiments of the invention can be implemented as a standalone application, a standalone application with custom integration support, or as part of a cloud based subscription service.

Embodiments of the invention can be implemented as an enterprise tool that can facilitate communications within or across organizations. Consumers of such a tool would be healthcare organizations that need effective communications among providers of care and delivery or relevant notifications and clinical alerts.

Provider-to-provider communication though the system is expected to improve workflow efficiency and patient care. Provider-to-patient communication though the system is expected to improve workflow efficiency, patient care, and customer satisfaction. Providers can communicate with each other or with patients through clicking on names in list that represents the provider graph. Users can access these lists through notifications (172 in FIG. 3), provider timeline (168 in FIG. 3), viewing now (168 in FIG. 3), patient lists (162 in FIG. 3), provider lists (164 in FIG. 3), or patient search (176 in FIG. 3). Once a provider is selected, contact information is presented and the user has the ability to communicate through one of the integrated modes (e.g. chat, message, email, phone, etc.).

The data contained within the system can also be used for research and analytics projects to determine how providers interact with each other and with each individual information system.

In general, it will be apparent to one of ordinary skill in the art that some of the embodiments as described hereinabove may be implemented using software, firmware, and/or hardware. The software code or specialized control hardware used to implement some of the present embodiments is not limiting of the present invention. For example, the embodiments described hereinabove may be implemented in computer software using any suitable computer software language. Such software may be stored on any type of suitable non-transitory computer-readable medium or media such as, for example, a magnetic or optical storage medium. Thus, the operation and behavior of the embodiments are described without specific reference to the actual software code or specialized hardware components. It is understood that artisans of ordinary skill would be able to design software and control hardware to implement the embodiments of the present invention based on the description herein with only a reasonable effort and without undue experimentation.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these sorts of focused discussions would not facilitate a better understanding of the present invention, and, therefore, a more detailed description of such elements is not provided herein.

In various embodiments of the present invention disclosed herein, a single component may be replaced by multiple components, and multiple components may be replaced by a single component, to perform a given function or functions. Except where such substitution would not be operative in practical embodiments of the present invention, such substitution is within the scope of the present invention.

While several aspects of the invention have been described herein, it should be apparent, however, that various modifications, alterations and adaptations to those aspects may occur to persons skilled in the art with the attainment of some or all of the advantages of the present invention. The disclosed embodiments are therefore intended to include all such modifications, alterations and adaptations without departing from the scope and spirit of the present invention.

What is claimed is:

1. An apparatus programmed for processing healthcare information, the apparatus comprising:
an electronic computer processor;
an electronic screen display operatively associated with the processor, the processor programmed for:
displaying data associated with a patient on the screen display, and
navigating from a first screen to a second screen displayed on the screen display, wherein only one screen is visible on the screen display at any point in time, in response to receiving a manual swipe on the screen display from a user; and
the processor further programmed to:
receive data from across multiple computer systems containing information associated with the selected patient data,
capture data associated with multiple events associated with the selected patient data from the multiple computer systems, wherein the events include a plurality of micro-events,
display on the screen display:
a list of providers associated with the selected patient data,
at least one graph representative of an interaction between two or more of the multiple computer systems and the selected patient data, wherein at least one of the interactions describes a relationship between a plurality of providers and the selected patient data,
data indicative of provider availability within a clinical situation involving provider data stored in the multiple computer systems,
a graphical representation of at least one latent tie associated with provider data contained in the multiple computer systems and the selected patient data, wherein the latent tie exists in a deactivated state until the latent tie is activated by receiving data indicating communication between or among at least a portion of the providers,
a graphical representation of at least one direct tie associated with provider data contained in the multiple computer systems and the selected patient data, wherein the direct ties and the latent ties are either permanent or transient for a period related to a specific episode of care, and a graphical representation of at least one meta-event associated with occurrence of a plurality of the captured micro-event data, follow across multiple communication platforms and adjust a preferred communication mode according to a currently utilized device associated with the selected patient data, capture at least a portion of the patient data through multiple external interfaces associated with the multiple computer systems, receive at least a portion of the patient data from at least one application specific listener programmed to translate application events to at least one of the external interfaces, and, connect, through a load balanced web farm, to a highly available database through a database interface for accessing at least a portion of the patient data.

2. The apparatus of claim 1, further comprising the processor programmed to:

weight a relationship between the selected patient data and provider data stored in the multiple computer systems; and display a presence band on the screen display in response to the weighted relationship data.

3. The apparatus of claim 2, wherein the displayed presence band represents at least one of a critical state, a related state, or an unrelated state associated with the patient data.

4. The apparatus of claim 1, wherein the communication platform is a mobile platform, a desktop platform, or a web platform.

5. The apparatus of claim 1, further comprising the processor programmed to determine the direct ties and the latent ties based on provider roles and patient conditions.

6. The apparatus of claim 1, further comprising the processor programmed to display on the screen display a graphical representation of a trust network among the providers who are accountable for actions of each other.

7. The apparatus of claim 1, further comprising the processor programmed to facilitate communication between or among different providers in response to at least a portion of the patient data.

8. The apparatus of claim 1, further comprising the processor programmed to generate at least one patient-centered graphical representation in response to at least a portion of the patient data.

9. The apparatus of claim 8, further comprising the processor programmed to generate the patient-centered graphical representation through detection and analysis of at least one indirect interaction with a patient.

10. A computer-implemented method for processing healthcare information, the method comprising:

receiving data from across multiple computer systems containing information associated with selected patient data;

capturing data associated with multiple events associated with the selected patient data from the multiple computer systems, wherein the events include a plurality of micro-events; and displaying on an electronic screen display:

a list of providers associated with the selected patient data, at least one graph representative of an interaction between two or more of the multiple computer systems and the selected patient data, wherein at least one of the interactions describes a relationship between a plurality of providers and the selected patient data, data indicative of provider availability within a clinical situation involving provider data stored in the multiple computer systems, a graphical representation of at least one latent tie associated with provider data contained in the multiple computer systems and the selected patient data, wherein the latent tie exists in a deactivated state until the latent tie is activated by receiving data indicating communication between or among at least a portion of the providers, a graphical representation of at least one direct tie associated with provider data contained in the multiple computer systems and the selected patient data, wherein the direct ties and the latent ties are either permanent or transient for a period related to a specific episode of care, and a graphical representation of at least one meta-event associated with occurrence of a plurality of the captured micro-event data;

following across multiple communication platforms and adjusting a preferred communication mode according to a currently utilized device associated with the selected patient data;

capturing at least a portion of the patient data through multiple external interfaces associated with the multiple computer systems;

receiving at least a portion of the patient data from at least one application specific listener programmed to translate application events to at least one of the external interfaces; and, connecting, through a load balanced web farm, to a highly available database through a database interface for receiving at least a portion of the patient data.

11. The method of claim 10, further comprising:

weighting a relationship between the selected patient data and provider data stored in the multiple computer systems; and displaying a presence band on the screen display in response to the weighted relationship data.

12. The method of claim 11, further comprising displaying a presence band representing at least one of a critical state, a related state, or an unrelated state associated with the patient data.

13. The method of claim 10, wherein the communication platform is a mobile platform, a desktop platform, or a web platform.

14. The method of claim 10, further comprising determining at least one direct tie or at least one latent tie based on provider roles and patient conditions.

15. The method of claim 10, further comprising displaying on the screen display a graphical representation of a trust network among the providers who are accountable for actions of each other.

16. The method of claim 10, further comprising facilitating communication between or among different providers in response to at least a portion of the patient data.

17. The method of claim 10, further comprising generating at least one patient-centered graphical representation in response to at least a portion of the patient data.

18. The method of claim 17, further comprising generating the patient-centered graphical representation through detection and analysis of at least one indirect interaction with a patient.

* * * * *